(12) United States Patent
Arnshav

(10) Patent No.: US 6,266,999 B1
(45) Date of Patent: Jul. 31, 2001

(54) METHOD AND APPARATUS FOR MEASURING THE PERMEABILITY TO WATER OF PERVIOUS SHEETS

(75) Inventor: Sivert Arnshav, Saltsjö-Boo (SE)

(73) Assignee: AB Lorentzen & Wettre, Kista (SE)

( * ) Notice: Subject to any disclaimer, the term of this patent is extended or adjusted under 35 U.S.C. 154(b) by 0 days.

(21) Appl. No.: 09/268,652

(22) Filed: Mar. 16, 1999

(30) Foreign Application Priority Data

Apr. 23, 1998 (SE) ................................................ 9801434

(51) Int. Cl.⁷ ................................................ G01N 15/08
(52) U.S. Cl. ................................................ 73/38
(58) Field of Search ................................ 73/38; 8/149.1; 162/198, 263; 239/417

(56) References Cited

U.S. PATENT DOCUMENTS

| | | |
|---|---|---|
| 2,722,837 | 11/1955 | Dwyer . |
| 3,091,123 | 5/1963 | Locke . |
| 3,397,319 | 8/1968 | Locke . |
| 3,577,767 | 5/1971 | Stedile . |
| 4,385,517 | 5/1983 | Sorce et al. . |
| 4,408,721 | * 10/1983 | Cohen et al. ........................ 239/417 |
| 4,880,499 | * 11/1989 | Pikulik ................................ 162/198 |
| 5,588,170 | * 12/1996 | Strahm ................................ 8/149.1 |
| 5,725,737 | * 3/1998 | Pikulik et al. ...................... 73/38 X |

FOREIGN PATENT DOCUMENTS 1292891    12/1991   (CA) .

* cited by examiner

Primary Examiner—Hezron Williams
Assistant Examiner—Jay L. Politzer
(74) Attorney, Agent, or Firm—Browdy and Neimark (57) ABSTRACT

A method for the measurement of the permeability to water of a pervious sheet material (16) comprising the steps of placing a nozzle means (5) against one surface of said sheet material (16) and flowing water through the nozzle means (5), characterized by maintaining a constant water flow through the nozzle means (5) and measuring the pressure of the constant water flow in the nozzle means (5). Optionally, a gas, such as air, is introduced into the water flow.

An apparatus for performing the method, comprising means (1) for supplying a constant water flow, nozzle means (5) for the constant water flow and means (6) for measuring the pressure of the constant water flow within the nozzle means (5). The apparatus optionally also comprises means (8) for introducing a gas, such as air, into the liquid flow.

22 Claims, 6 Drawing Sheets

FIG.1

FORMING FABRIC PERMEABILITY TESTER

FIG. 2

FORMING FABRIC PERMEABILITY TESTER

METHOD AND APPARATUS FOR MEASURING THE PERMEABILITY TO WATER OF PERVIOUS SHEETS

BACKGROUND OF THE INVENTION

1. Technical Field of the Invention

The present invention relates to a method and apparatus for measuring the permeability to water of pervious sheets. More specifically, it relates to a method and apparatus for measuring the permeability to water of pervious sheets such as forming fabrics (also referred to as wires) and press felts as used in paper, board and pulp production processes.

2. Prior Art

In paper and board production plants, pervious sheets such as felts and forming fabrics are used for dewatering of aqueous suspensions of the pulp fibers in the production of paper and board. The permeability to water of these sheets is an important factor to the production efficiency as well as to the quality of the product obtained. Methods and apparatuses for evaluating this factor accordingly have been sought.

Some instruments of the prior art make use of the measurement of the flow rate of a stream of air through the pervious sheet used in the paper machine, see e.g. U.S. Pat. Nos. 2,722,837; 3,091,123 and 3,397,319. However, it is highly questionable whether the measurement of the permeability to air could provide an accurate measurement of the felt or forming fabric performance, as this is related not to the permeability to air but to water. Moreover, as taught in the Canadian patent no 1,292,891, this instrumentation of the prior art suffers from a poor reproducibility.

In view of this, instruments for the measurement of the water permeability by use of a flow of water have been developed. The first ones of this type of instruments were of a stationary nature and were used in laboratory measurements, see e.g. the U.S. Pat. Nos. 3,577,767 and 4,385,517. To be able to make a measurement of the permeability to water of a pervious sheet used on a paper machine, one thus had to cut out a sample piece and take it to the laboratory. This obviously excludes the method from being applicable in an on-line mode, such as would be desirable from a production efficiency point of view.

Consequently, in the art a need still existed for a method and apparatus for measuring the permeability to water of a pervious sheet on a paper machine in an on-line mode, to be able to quickly ascertain the performance of the pervious sheet, without having to destroy it such as by cutting out a piece of it. This was the object of the Canadian patent no 1,292,891, wherein a method and an apparatus for measuring the permeability to water of a pervious sheet material are disclosed. The method taught in this patent can be used in a dynamic mode, i.e. on a pervious sheet material, such as a press felt or a forming fabric in rapid movement in the paper machine, and consists of measuring the flow of a stream of water injected at constant pressure through the material. Thus, this document discloses placing a nozzle against one surface of the material, flowing water through said nozzle at a pressure between 2 kPa and 1000 kPa and measuring the rate of flow of the water. A commercially available instrument operating according to this principle is the SCANPRO FELT-PERM™, manufactured and sold by Lorentzen & Wettre, of Sweden.

This measuring method as taught in said Canadian patent, while being optimized for measuring the permeability to water of a pervious sheet material such as a press felt, is less adequate for measuring the permeability to water of a pervious sheet material of the type of a forming fabric. Indeed, the properties of a forming fabric differ substantially from those of a press felt. The former is a loose woven gauze of rather coarse plastic threads and very permeable to water, while the latter is a close woven structure of a much lower permeability to water. It thus has been found that the dynamics of the measurement signal is inadequate when using the method based on measuring the flow of water at constant pressure to assess the permeability of a forming fabric, i.e. the flow rate varies only negligibly in response to the variation of permeability. As a result, the method will not give an adequate indication of the degree of wear and clogging of the forming fabric.

Moreover, in the instrumentation according to the Canadian patent, the nozzle ranges from 1 to 4 mm in diameter, and the pressure of injection of the water ranges from 2 to 1000 kPa. While being suitable for measuring the permeability of a press felt, the high pressure, small diameter water jet produced, in the case of a forming fabric will lead to a local cleaning away of fibers caught onto the surface of the fabric and this in turn will result in an uneven dewatering of the pulp on the thus locally cleaned forming fabric.

GENERAL DESCRIPTION OF THE INVENTION

According to an aspect of the present invention there is provided a method of measuring the permeability to water of pervious sheet materials.

An aspect of the present invention thus is to provide a method for the measurement of the permeability to water of a pervious sheet material comprising the steps of placing a nozzle against one surface of said sheet material and flowing water through the nozzle, wherein a constant water flow is maintained through the nozzle and the pressure of the water flow in the nozzle is measured. This will result in the advantage of providing a measurement signal of a better dynamics, i.e. being more sensitive to the variation in permeability of the material on which the measurement is performed, due to the fact that the pressure within the water flow varies to a greater extent than the flow rate as a function of the permeability of the material.

According to a further aspect of the present invention, the method is performable on a pervious sheet such as a press felt or forming fabric in a paper making machine while the machine is running, i.e. by an on-line measurement. This will provide the advantage of being able to control as often as desired the efficiency of the pervious sheet in the dewatering process in the paper machine without having to interrupt the production.

According to still a further aspect of the invention, a gas such as air is introduced into the water flow. The introduction of air into the water flow will result in a water jet of reduced density, and an advantageous effect of this will be that the washing effect of the water flow on the pervious sheet material will be reduced. As noted herein above, a localized washing away of contaminating material, such as fibers, tends to result in an uneven cleaning of the pervious sheet material, which is not desirable for the obtention of a uniform behaviour of the sheet material across the totality of the surface thereof.

It has been found that at lower flow rate of the water, the measurement signal has an undesirable tendency of becoming dependent of the velocity of the pervious sheet running in the paper machine. However, increasing the water flow rate will result in an increased consumption of water, which may be not desirable e.g. in the case of a portable apparatus comprising a portable reservoir for the water to be used in the method. By introducing air into the water flow, a reduction of the viscosity of the flowing water will be obtained and an enhanced flow rate will result for the jet exiting the nozzle, leading to the advantageous effect of reducing the dependency of the velocity of the pervious sheet movement.

It also has been found that by introducing air into the water flow, a measurement signal of further enhanced dynamics will be obtainable.

According to another aspect of the present invention there is provided an apparatus for use in a method of the invention, also as specified in the claims.

According to a further aspect of the present invention, the apparatus may be used as a portable device or as a fixed installation e.g. in a paper mill.

BRIEF DESCRIPTION OF THE DRAWINGS

A number of embodiments of the invention will now be described in detail with reference to the figures in the drawings, wherein.

DETAILED DESCRIPTION OF THE PREFERRED EMBODIMENTS(S) OF THE INVENTION

Figure 1:
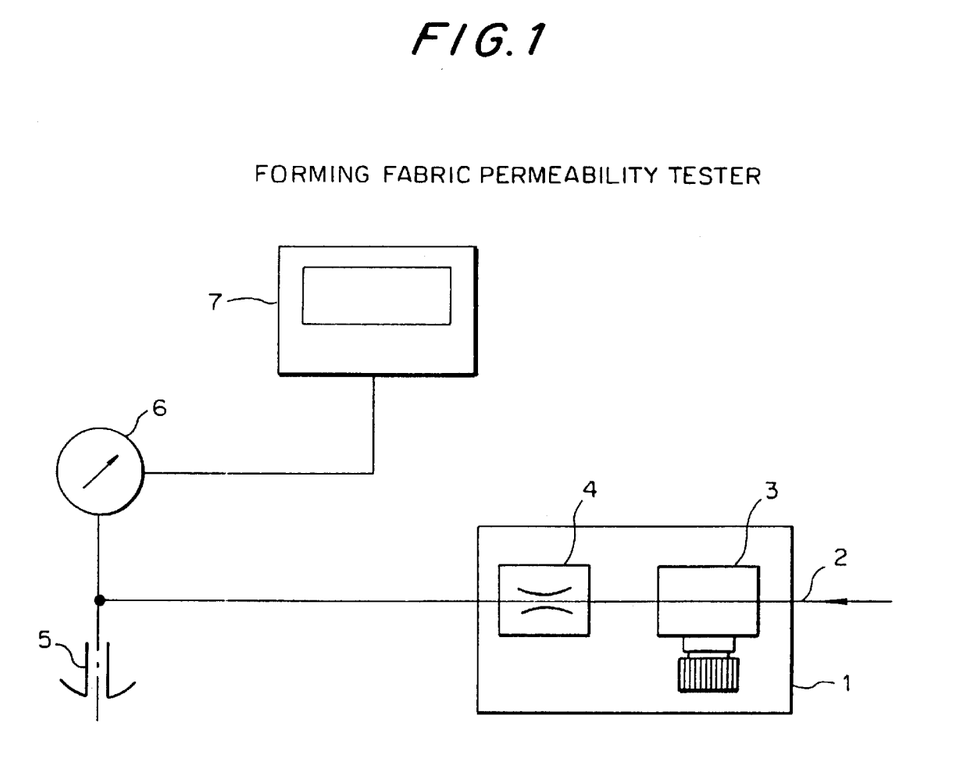
FIG. 1 is a schematic diagram representing the main parts of an apparatus according to the invention.

The apparatus represented in FIG. 1 comprises a constant flow device 1 to which water is supplied through a line 2.

The constant flow device 1 comprises a pressure regulator 3 and a flow regulator 4, the former providing a specified pressure to the water flowing into the latter, such as from 50 kPa to 1000 kPa, more preferably from 100 kPa to 600 kPa. By means of the flow regulator 4, the volume rate of flow of the water may be regulated to a desired value, such as from 5 to 100 ml/sec, preferably from 20 to 50 ml/sec.

The constant flow device 1 is coupled through the water flow line 2 to a nozzle 5, the latter further being coupled to a pressure gauge 6, also referred to as permeability gauge. The permeability gauge 6 registers the pressure of the water within the nozzle 5, the registered values optionally being transmitted to a recording device 7. The pressure values registered within the nozzle 5 usually are from 0 to 100 kPa.

The nozzle 5 has an outlet orifice diameter of 2–15 mm, preferably 3–7 mm. It preferably is of a shape suitable for giving a tight seal towards the sheet material when held against it, without causing any damage to the sheet material.

As an example, the nozzle 5 orifice may be of a rounded outer shape, having rounded, somewhat protruding edges.

In performing a method according to the invention for measuring the permeability of a pervious sheet material, such as a press felt or a forming fabric in e.g. a paper machine, the nozzle 5 is pressed onto the sheet material and water is passed through the nozzle at a constant flow rate. The nozzle may be held immobile against the pervious sheet material or may be moved across it, while the pervious sheet material in turn may be at rest or running in the paper machine.

The volume rate of flow of the water through the nozzle 5 in general is from 5 to 100 ml/sec, preferably from 20 to 50 ml/sec.

Water may be supplied to the apparatus either from a water tank, using a pumping device, or directly from a water distribution system, such as the municipal system.

Figure 2:
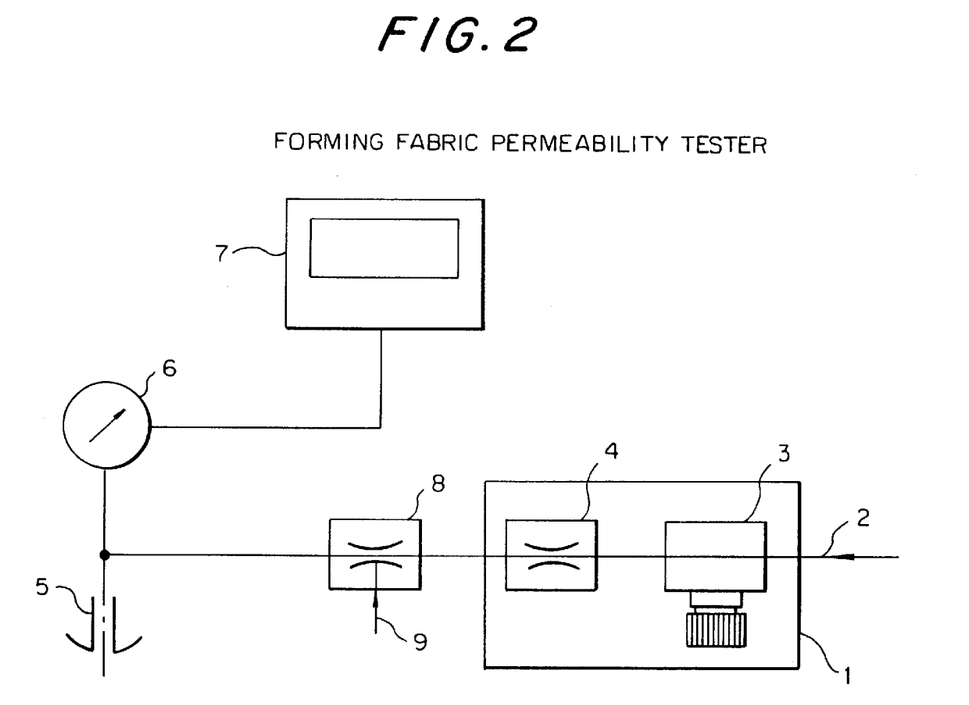
FIG. 2 is a schematic diagram representing the main parts of another apparatus according to the invention.

In an embodiment of the invention, especially preferred in the case of the pervious sheet material being a forming fabric, an apparatus as represented in FIG. 2 is used. This apparatus comprises, in addition to the elements of the apparatus as represented in FIG. 1, means 8 for introducing gas, such as air, into a liquid flow, such as the flow of water used in the method of the invention. The means 8 for introducing gas will in the description herein below be referred to as an air injector, air being a preferable gas in the present method for cost and availability reasons. The air injector 8 may be situated on the water flow line 2, between the constant flow device 1 and the nozzle 5, or may be integrated in the flow regulator 4 of the constant flow device 1.

Figure 3:
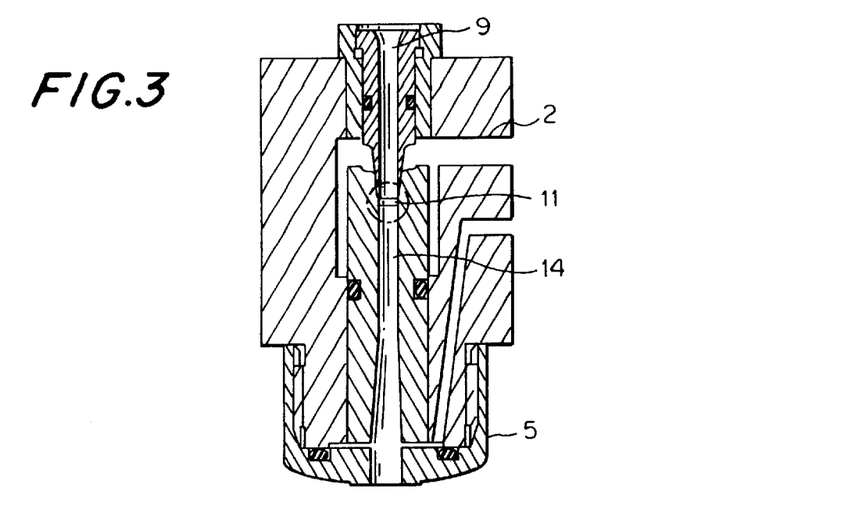
FIG. 3 represents a sectional view of a means for introducing air into the flow of water, coupled to a nozzle of an apparatus according to the invention.
Figure 3A:
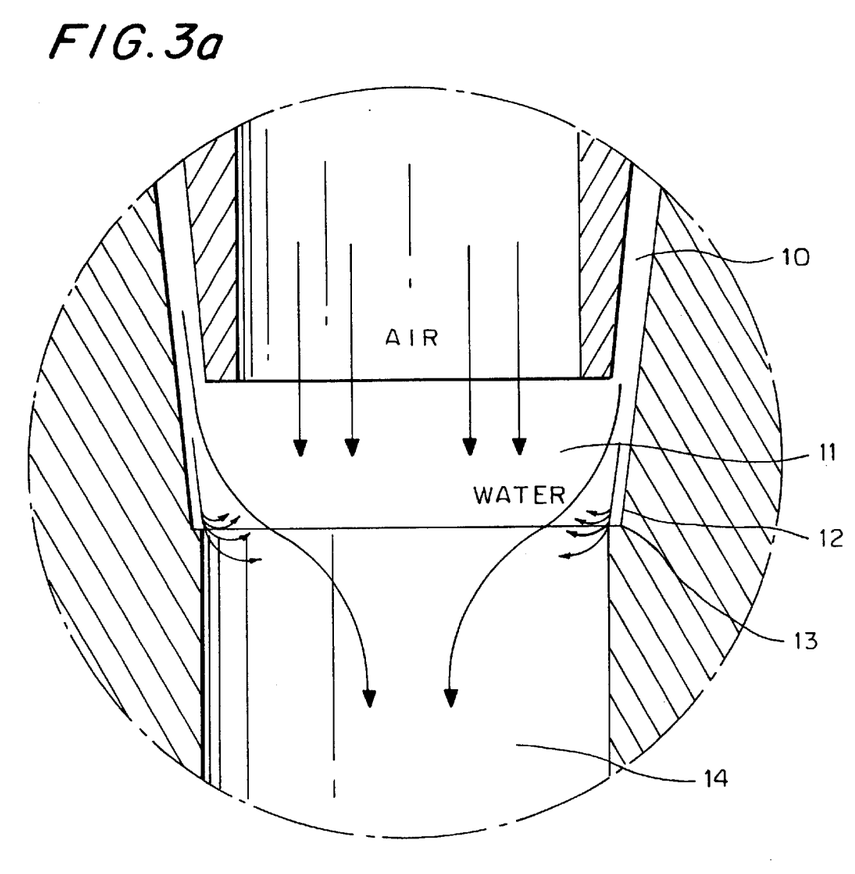

A preferred embodiment of the air injector 8 is represented in FIG. 3. The air injector 8 as represented in FIG. 3 comprises an inlet duct 9 for air surrounded by a preferably annular opening 10 for the flow of water in the line 2, both debouching in a mixing zone 11 for the air and the flow of water.

In the scaled area of FIG. 3 a preferred configuration of the air injector 8 is shown, comprising a radial constriction in the mixing zone 11. The profile of the inner wall 12 of the air injector 8, comprises an annular edge 13 corresponding to the constriction.

The water flow entering from line 2 through the annular opening 10 at a high flow rate hits the annular edge 13. As a result, an air venturi effect is obtained, whereby air is entrained through the inlet duct 9 into the flow of water. Mixing zone 11 is followed by a conduit 14, through which the flow of water and air reaches the nozzle 5.

Figure 4:
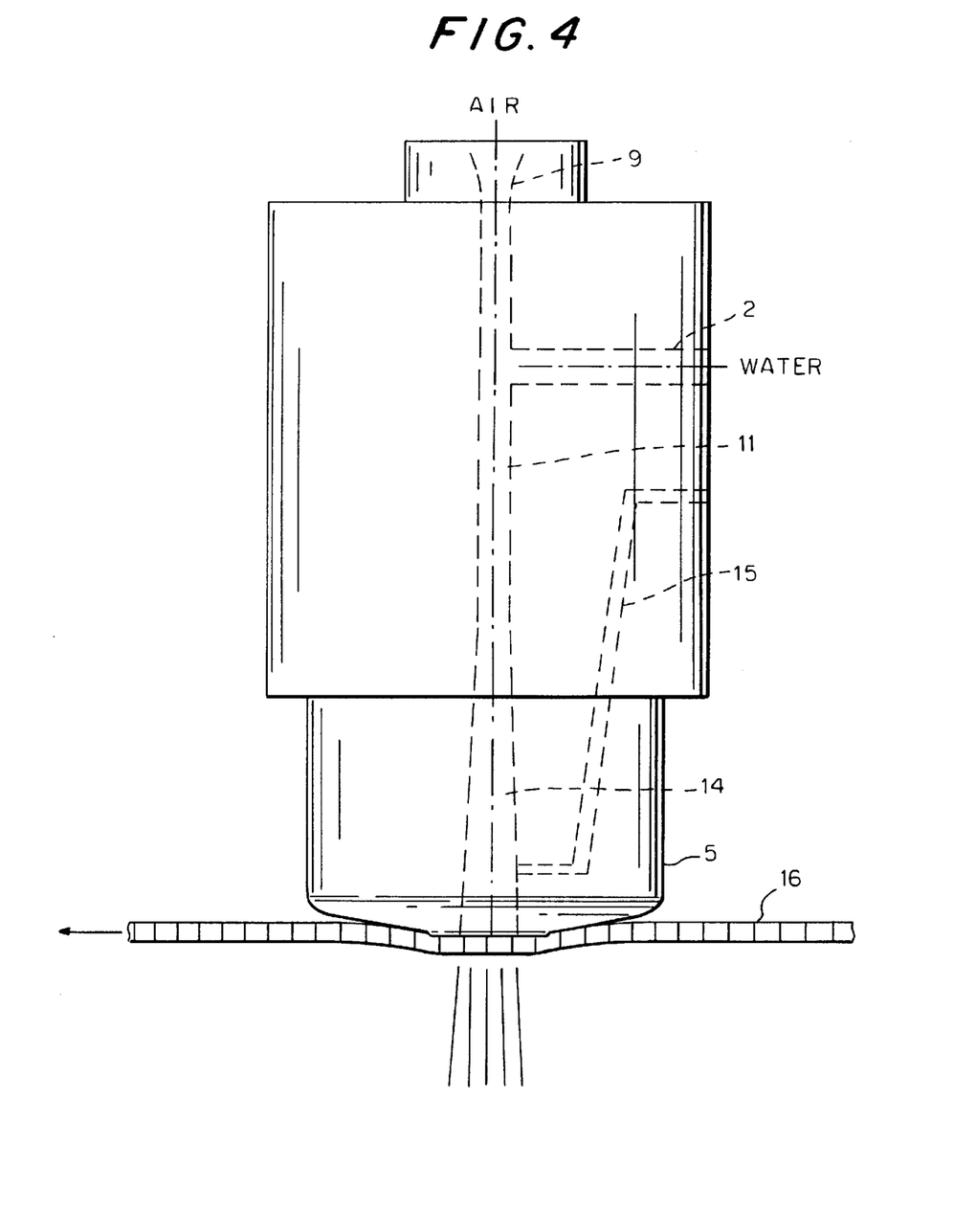
FIG. 4 represents a view of a means for introducing air into the flow of water coupled to a nozzle of an apparatus of the invention, in use in a method of measuring the permeability of a running forming fabric.

In FIG. 4 the air injector 8 coupled to the nozzle 5 is represented as used in a method of measuring the permeability of a pervious sheet material 16, here a running forming fabric. By the channel 15, the interior of the nozzle 5 is connected to the pressure gauge 6. The pressure of the flow of water and air within the nozzle 5 thus may be continuously measured, the pressure varying as a function of the permeability to water of the forming fabric 16. As seen from the FIG. 4, in performing the measurement, the nozzle 5 is held tightly against the forming fabric 16, and a mixture of water and air is made to flow through the nozzle 5 orifice. The nozzle 5 may be moved over the running forming fabric 16, e.g. in a direction sensibly transverse to the run direction of the forming fabric 16.

Figure 5:
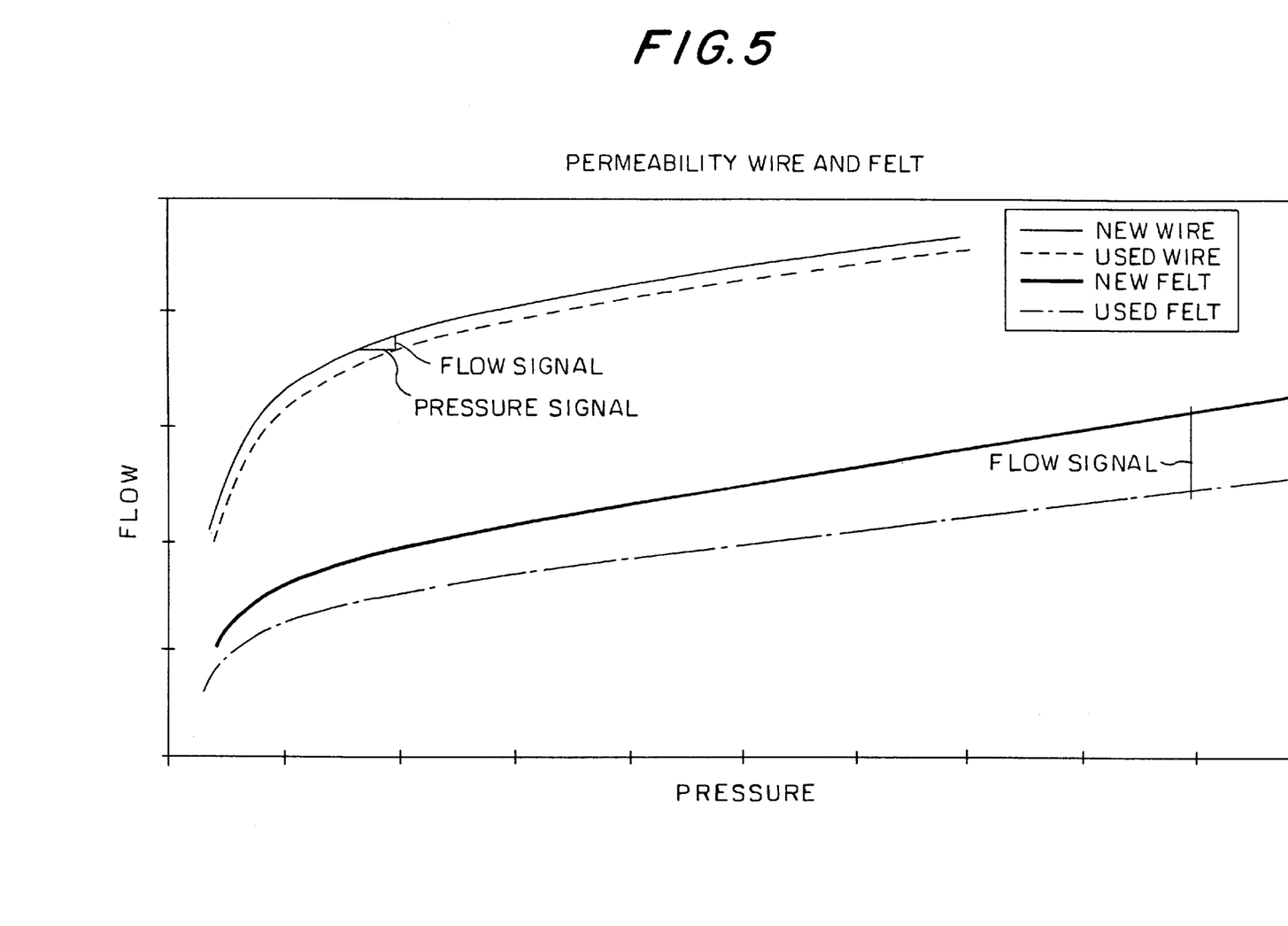
FIG. 5 represents the flow through a nozzle measured at constant pressure vs. the pressure in the nozzle measured at constant flow through the nozzle, by measurements performed on a new and a used wire and felt, respectively.

FIG. 5 represents the use of pressure measurement at constant flow vs. the use of flow measurement at constant pressure as a way of measuring the permeability of a pervious sheet material. The two upper curves in FIG. 5 show the flow vs. pressure signal of a new forming fabric (wire) and a used forming fabric, respectively, whereas the two lower curves show the flow vs. pressure signal of a new press felt and a used press felt respectively. From FIG. 5 it can be seen that over most of the pressure and flow range, except for the very low range of values of pressure and flow, the pressure variation is higher than a corresponding flow variation, this being true for both the press felt and the forming fabric material. FIG. 5 thus illustrates the superiority of measuring the pressure at a constant flow as an indication of the permeability of a pervious sheet material.

Figure 6:
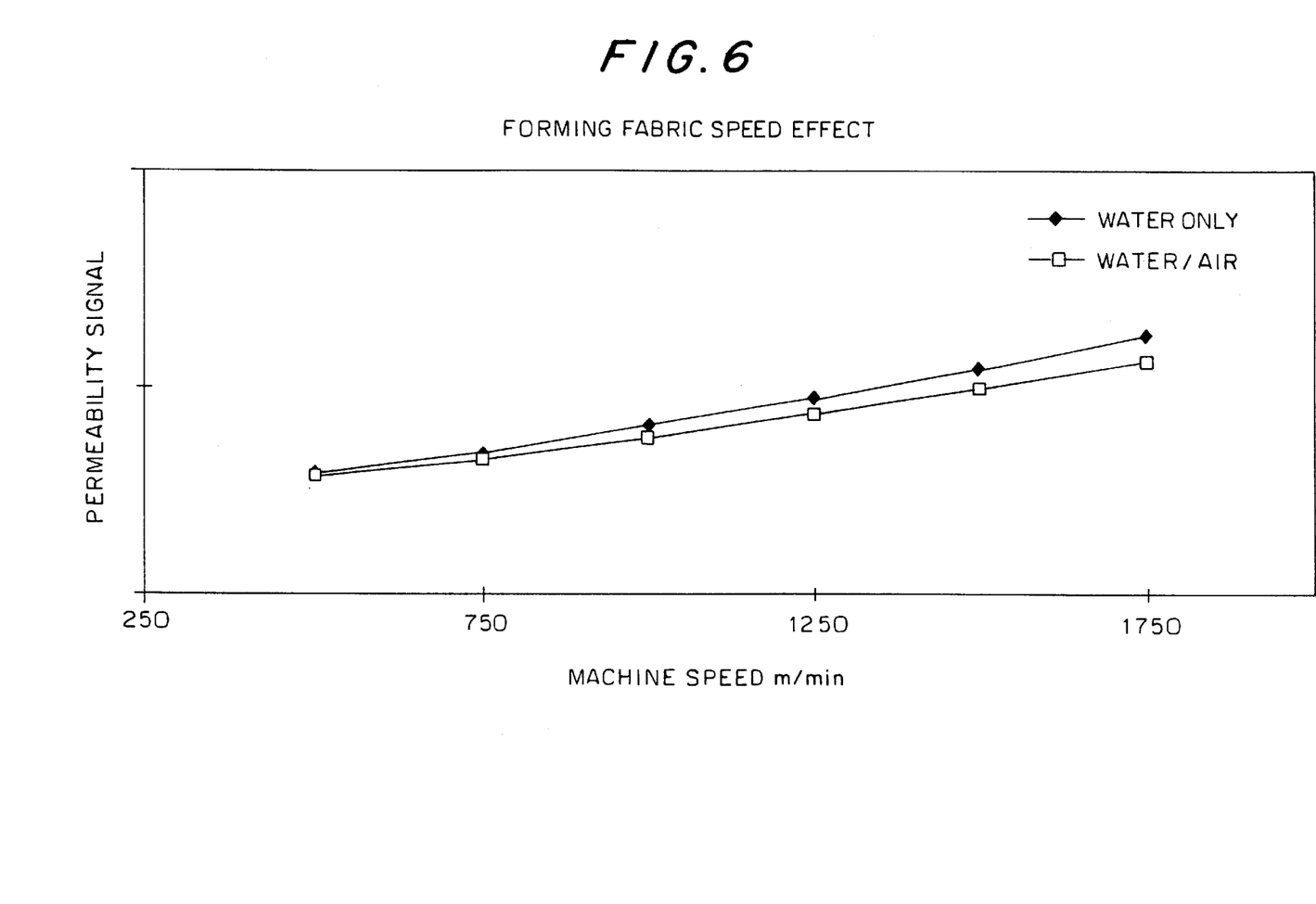
FIG. 6 represents the measured value of the permeability signal as a function of the machine speed, in a method using a flow of water and a method using a flow of water and air, respectively.

FIG. 6 represents the measured permeability signal as a function of the machine speed. As noted herein above, at a lower flow rate of the water, the measurement signal has a tendency of becoming dependent of the velocity of the pervious sheet running in the paper machine. Indeed, at increasing machine speed the permeability signal measured is substantially greater than the one measured at lower machine speed. One way of avoiding this biasing effect would be to use a higher volume rate of flow of water. This, however also will result in a higher water consumption, a particularly serious drawback in the case of a portable device comprising a portable water reservoir. By introducing air into the flow of water, to obtain a mixed flow of water and air, the consumption of water may be reduced by as much as e.g. 15%.

By use of the method and apparatus of the invention, the degree of wear and clogging of a pervious sheet material such as a press felt or a forming fabric in a paper machine may be monitored in a convenient way with an increased degree of sensitivity.

Moreover, the apparatus may be used on a pervious sheet material such as a press felt or a forming fabric in a paper machine for specifically determining the areas in need of cleaning.

After cleaning the pervious sheet material, the satisfactory result of the cleaning procedure may be checked by measuring again the permeability of the thus cleaned material.

Furthermore, in the development and production of new pervious sheet materials, the method and apparatus may be used to investigate the dewatering capacity of the material.

The apparatus may be portable as well as a fixed installation in e.g. a paper machine, e.g. mounted on an overhead travelling crane, or on an arm or bar extending into the paper machine.

What is claimed is:

1. An apparatus for the measurement of the permeability to water of a pervious sheet material (16) comprising;
   means (1) for supplying a constant water to a liquid flow line (2);
   nozzle means (5) for the constant water flow;
   means (6) for measuring the pressure of the constant water flow within the nozzle means (5); and
   a means (8) for introducing gas into the flow of water in said liquid flow line (2), comprising an inlet duct (9) for said gas surrounded by an opening (10) for the liquid flow line (2), debauching in a mixing zone (11), an annular edge (13) being provided in the mixing zone (11) whereby gas is entrained from the inlet duct (9) (2).

2. The apparatus according to claim 1, wherein the means (1) for supplying a constant water flow comprises means (3) for regulating the pressure of a flow of water and means (4) for regulating the volume rate of flow of the water.

3. The apparatus according to claim 2, wherein the nozzle means (5) comprises an outlet orifice having a diameter of 2–15 mm.

4. The apparatus according to claim 1, wherein the nozzle means (5) comprises an outlet orifice having a diameter of 2–15 mm.

5. The apparatus of claim 1 wherein the mixing zone (11) is of a geometry providing a venturi effect in the vicinity of the orifice of the inlet duct (9) for the gas so as to entrain gas from the inlet duct (9) into the water flow.

6. The apparatus of claim 4, wherein the diameter of the outlet orifice is preferably 3–7 mm.

7. The apparatus of claim 1, wherein the diameter of the outlet orifice is preferably 3–7 mm.

8. The apparatus according to claim 1, wherein the opening for the flow of water is annular.

9. In a method for the measurement of the permeability to water of a pervious sheet material, which method provides a reduced washing effect of the water flow on the pervious sheet material and a permeability measurement of enhanced dynamics, comprising the steps of:
   1) regulating a flow of water in a water line to produce a flow of water having a constant volume rate of flow;
   2) introducing a gas into the water flow to obtain a mixture of the water flow having a constant volume rate of flow and gas;
   3) providing the mixture of the gas and the water flow having a constant volume rate of flow through the water line to a nozzle;
   4) placing the nozzle against one surface of the pervious sheet material; and
   5) measuring the permeability of the pervious sheet material by measuring the pressure of the mixture of the water flow having a constant volume rate of flow and gas in the nozzle.

10. The method according to claim 9, in a process for forming paper, wherein said sheet material is a press felt or forming fabric in a paper making machine.

11. The method according to claim 10, comprising introducing a gas into the water flow.

12. The method according to claim 9, wherein the constant volume rate of flow is selected at a value from 5 to 100 ml/sec.

13. The method according to claim 9, wherein the pervious sheet material (16) is a forming fabric.

14. The method according to claim 9, wherein the constant volume rate of flow is selected at a value from 20 to 50 ml/sec.

15. The method according to claim 9, in a process for forming paper, wherein said sheet material is a forming fabric in a paper machine.

16. The method according to claim 9, wherein said gas is air.

17. In a method for the measurement of the permeability to water of a pervious sheet material providing a reduced washing effect of the water flow on the pervious sheet material and a permeability measurement of enhanced dynamics, comprising the steps of:
   1) regulating a flow of water in a water line to produce a flow of water having a constant volume rate of flow;
   2) introducing a gas into the water flow by using a means (8) for introducing gas into the flow of water in the liquid flow line (2), comprising an inlet duct (9) for the gas surrounded by an opening (10) for the liquid flow line (2), debouching in a mixing zone (11), an annular edge (13) being provided in the mixing zone (11) whereby gas is entrained from the inlet duct (9) into the liquid flow line (2) to obtain a mixture of the water flow having a constant volume rate of flow and gas;

3) providing the mixture of the water flow having a constant volume rate of flow and gas through the water line to a nozzle;

4) placing the nozzle against one surface of the pervious sheet material; and 5) measuring the permeability of the pervious sheet material by measuring the pressure of the mixture of the water flow having a constant volume rate of flow and gas in the nozzle.

18. The method according to claim 17, wherein the constant volume rate of flow is selected at a value from 5 to 100 ml/sec.

19. The method according to claim 17, wherein the previous sheet material (16) is a forming fabric.

20. The method according to claim 17, wherein he constant volume rate of flow is selected at a value from 20 to 50 ml/sec.

21. The method according to claim 17, in a process for forming paper, wherein said sheet material is a forming fabric in a paper machine.

22. The method according to claim 17, wherein said gas is air.

* * * * *